United States Patent [19]

Grier et al.

[11] 4,335,141
[45] Jun. 15, 1982

[54] 2-SUBSTITUTED-AMINOPROPENE-AND PROPANENITRILE ANTIMICROBIAL AND ANTI-INFLAMMATORY AGENTS

[75] Inventors: Nathaniel Grier, Englewood; Richard A. Dybas, Somerville; Bruce E. Witzel, Rahway, all of N.J.

[73] Assignee: Merck & Co., Inc., Rahway, N.J.

[21] Appl. No.: 106,616

[22] Filed: Dec. 26, 1979

[51] Int. Cl.$^3$ ............... C07C 121/45; C07C 121/48; C07C 121/43; A61K 31/275
[52] U.S. Cl. .................................. 424/304; 260/464; 260/465 D; 260/465 E; 260/465.5 R; 260/465.4
[58] Field of Search ............ 260/465.5 R, 464, 465.4; 424/304

[56] References Cited

U.S. PATENT DOCUMENTS

2,211,152  8/1940  Nicodemus et al. ......... 260/465.5 R
4,074,051  2/1978  Stevens ........................ 260/465.5 R

FOREIGN PATENT DOCUMENTS

1242111  8/1971  United Kingdom .
1242112  8/1971  United Kingdom .
1242113  8/1971  United Kingdom .

OTHER PUBLICATIONS

C.A.; 76 (1972), 99594a, Adrian.
C.A.; 73, (1970), 99407e, Stevens.
Adrian; Bull. Soc. Chim. Fr., No. 11, (1971), pp. 4160–4169.
Adrian; C. R. Seances Acad. Sci., 272, (1971), pp. 494–496.
Dybas, et al.; Developments in Ind. Microbiology, 19, (1978), pp. 347–353.
Cyanamid, "The Chemistry of Acrylonitrile", 2nd ed., (1959), p. 10.

*Primary Examiner*—Joseph Paul Brust
*Attorney, Agent, or Firm*—Theresa Y. Cheng; Raymond M. Speer; Mario A. Monaco

[57] ABSTRACT

2-Substituted-aminopropene and propanenitriles of the formula:

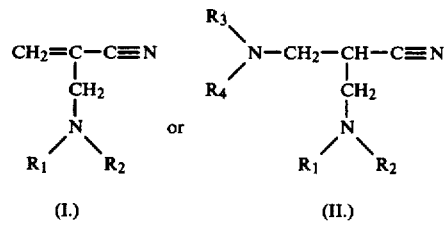

are effective antimicrobial agents (compounds of Formula II.), and potent anti-inflammatory agents of decreased acute toxicity (compounds of Formula I.).

10 Claims, No Drawings

4,335,141

2-SUBSTITUTED-AMINOPROPENE-AND PROPANENITRILE ANTIMICROBIAL AND ANTI-INFLAMMATORY AGENTS

BACKGROUND OF THE INVENTION

1. Field of the Invention

The present invention is concerned with novel 2-substituted-aminopropene-and propanenitriles; with antimicrobial compositions and their use in protecting industrial products and systems of a wide variety against the deteriorating action of bacteria and fungi; and with anti-inflammatory compositions and their use in treating pain, fever and inflammation.

2. Brief Description of the Prior Art

2-Substituted-aminopropenenitriles having alkyl substituents of six or less carbon atoms are known. See, for example, G. Adrian, *Bull. Soc. Chim. Fr.*, No. 11, pp. 4160–4169 (1971); *C. R. Seances Acad. Sci.*, 272, 494 (1971); and German Offenlegungschrift 1,965,872. However, unlike the compounds of the present invention, which always possess a higher alkyl substituent, the compounds of the prior art exhibit a high degree of mammalian toxicity and are only described as being useful in the preparation of polymers. See also Dybas et al., *Developments in Industrial Microbiology*, Vol. 19, pp. 347–353 (1978), which discloses 2-[(dimethylamino)methyl]-2-propenenitrile and 2-[(di-n-butylamino)methyl]-2-propenenitrile having antimicrobial activity. Again, however, these compounds exhibit a high degree of mammalian toxicity, unlike the compounds of the present invention.

SUMMARY OF THE INVENTION

In accordance with the present invention there is provided novel compounds of the formula:

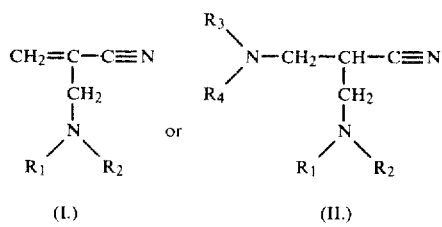

wherein:

$R_1$ is straight or branched $C_8$–$C_{20}$ alkyl; and $R_2$, $R_3$, and $R_4$ are independently selected from the group consisting of hydrogen; straight or branched $C_1$–$C_{20}$ alkyl; hydroxy $C_{1-4}$ alkyl; $C_{1-4}$ alkoxy $C_{1-4}$ alkyl; halo $C_{1-4}$ alkyl; carboxy $C_{1-4}$ alkyl; $C_{1-4}$ alkoxycarbonyl $C_{1-4}$ alkyl; carboxamido $C_{1-4}$ alkyl; and $C_{3-8}$ cycloalkyl;

and acid addition and quaternary salts thereof.

Examples of preferred novel compounds of the present invention are:

2-[(N-n-octadecylamino)methyl]-2-propenenitrile
2-[(N-methyl-N-n-octadecylamino)methyl]-2-propenenitrile
2[(N-hexyl-N-n-pentadecylamino)methyl]-2-propenenitrile
2-{[N-(2-methoxyethyl)-N-n-octadecylamino]methyl}-2-propenenitrile
2-cyano-N,N'-dimethyl-N,N'-di(n-octadecyl)-1,3-propanediamine
2-cyano-N,N-dimethyl-N'-methyl-N'-n-octadecyl-1,3-propanediamine
2-cyano-N,N-di(2-hydroxyethyl)-N'-methyl-N'-n-octadecyl-1,3-propanediamine
2-cyano-N,N-dimethyl-N',N'-di(2-ethylhexyl)-1,3-propanediamine Both Formula I and Formula II compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides: dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention of Formula II are useful in the protection of aqueous systems such as aqueous paints, adhesives, pigment dispersions, emulsions, cooling tower waters, enhanced oil recovery brines and pusher fluids, papermill white water, and metal-working fluids against microbial deterioration.

For use, these compounds can be applied neat or employed in a diluted form. Satisfactory diluents include any inert material not destructive of the antimicrobial activity and especially liquid formulations comprising aqueous dispersions, solutions, and emulsions. Solid diluents include talc, corn starch, alumina and diatomaceous earth. The antimicrobial agents of this invention can also be deposed on materials such as natural fibers including paper, cotton, wool and synthetic fibers such as nylon, polypropylene, as well as upon inanimate surfaces including hard surfaces such as wood, glass, metal, tile, rubber, plastic, and porous surfaces such as concrete, leather and the like.

For agricultural uses, the compounds of Formula II are most suitably used in the form of aqueous suspensions or emulsions, the free base products being generally insoluble in water. For this type of formulation various powdered carriers can be employed to aid in achieving uniform distribution. Talc, fuller's earth, calcium silicate, calcium carbonate, clays and the like are admixed with the agent along with wetting and dispersing agents and sticking agents. For maximum chemical compatibility those which are non-ionic in character are preferred. Other anionic or cationic surfactants are also satisfactory.

In formulating the Formula II compounds for the above uses, the compounds can be employed in combination with other antimicrobial agents, surfactants, insecticides, defoamers, odorants, or as chelates of metals such as copper, calcium, magnesium and iron.

Two aqueous paints, an interior polyvinyl acetate and an exterior polyacrylic were studied as vulnerable substrates. An inoculum prepared from a 24 hour old broth culture of *Pseudomonas aeruginosa* ATCC 10145 was used at a rate of 1 ml. per 100 gm. of paint. The inoculated samples are incubated at 28°-30° C. and samples are assayed for microbial population densities after 24, 48, 72 hours and seven days by streaking on tryptone glucose extract agar plates. These plates are incubated at 28°-30° C. for seven days and examined for growth. Seven days after the first inoculation, the paints are reinoculated and the assay scheme repeated. Samples which are rendered sterile within 24-72 hours upon microbial challenge and which remain so after seven days and on repeat challenge are adequately protected.

Typical results indicate that the Formula II compounds of this invention containing 1-dimethylamino-3-(2,4,4-trimethylpentan-2-yl) and 3-(n-dodecyl)amino derivatives and others can produce sterility at concentrations of 0.01-0.1% by weight of both paints within 24-72 hours upon inoculation and reinoculation. Control paints containing no preservatives are completely degraded at the end of the two-week period.

The two aqueous paint systems have the compositions of Tables 1 and 2 and were selected as representative of the more commonly manufactured types. The addition of other agents including different thickeners, pigments and extenders, paint film antifungal agents, surfactants, etc., does not adversely affect the performance of the compounds invented herein.

TABLE 1

| PVA EXTERIOR (COMPOSITION - PARTS BY WEIGHT) | |
| --- | --- |
| Cowles dispenser: | |
| Water | 140 |
| Daxad 30, Na salt of polymerized carboxylic acid, W.R. Grace Co. | 6 |
| Potassium tripolyphosphate | 1 |
| Igepal Co-630, nonylphenoxypoly-(ethyleneoxy)ethanol, General Aniline & Film Co. | 1.5 |
| Polyethyleneglycol | 2 |
| Methylcellulose solution (3%) | 70 |
| Defoamer | 1 |
| 2(4'-thiazolyl)benzimidazole | 1 |
| Titanium dioxide | 250 |
| Disperse ten minutes at 4,800 r.p.m. | |
| Talc | 75 |
| Disperse ten minutes at 4,800 r.p.m. | |
| Reduction: | |
| Methylcellulose solution (3%) | 68.5 |
| Methyl carbitol | 30 |
| Ethylene glycol | 40 |
| Polyvinyl acetate emulsion | 425 |

TABLE 2

| INTERIOR ACRYLIC (COMPOSITION - PARTS BY WEIGHT) | |
| --- | --- |
| Cowles disperser: | |
| Water | 450 |
| Diethylene Glycol[1] | 30 |
| Methylcellulose, 4,000 cps[1] | 5 |
| Potassium tripolyphosphate | 1.66 |
| Lecithin | 4 |
| Defoamer | 3 |
| Titanium dioxide | 125 |
| Disperse ten minutes at 4,800 r.p.m. | |
| Talc | 250 |
| Calcium silicate | 5 |
| Disperse ten minutes at 4,800 r.p.m. | |
| Reduction: | |
| Acrylic resin emulsion | 208 |

[1]Premix diethylene glycol and methylcellulose prior to adding water.

Thus, in accordance with the present invention there is provided an antimicrobial composition comprising an inert solid carrier and an antimicrobially effective amount of a compound of the formula:

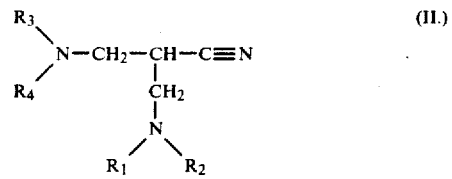

wherein $R_1$ through $R_4$ are as defined above, and acid addition and quaternary salts thereof.

In accordance with the present invention there is further provided anti-inflammatory compositions for use in treating pain, fever, and inflammation. The novel compounds of the present invention of Formula I possess a high degree of anti-inflammatory, analgesic and anti-pyretic activity. They are of value in the treatment of arthritic and dermatological disorders or like conditions responsive to anti-inflammatory drugs. In general they are indicated for a wide variety of conditions where one or more of the symptons of inflammation, fever and pain are manifested. Included within this category are diseases such as rheumatoid arthritis, osteo arthritis, gout, infectious arthritis and rheumatic fever. As indicated above the compounds utilized in the practice of the invention also possess a useful degree of analgesic and anti-pyretic activity.

Surprisingly, the propenenitrile compounds of Formula I appear to be devoid of significant antimicrobial action, especially as compared to the known loweralkylamino homologs. For example, 2-[(N-methyl-N-n-octadecylamino)methyl]-2-propenenitrile was ineffective at 0.2% concentration in preserving polyvinylacetate or polyacrylic paint challenged with *Psudomonas aeruginosa*, whereas 2-(dimethylaminomethyl)-2-propenenitrile and 2-[di(n-butyl)aminomethyl]-2-propenenitrile were protective at from 0.01 to 0.1% in polyvinylacetate paint and at 0.2% in polyacrylic paint. Moreover, the octadecylamino derivative referred to, at a loading of 2000 μg. in the agar overlay of a petri plate in the Ames bacterial mutagen test, was non-inhibitory to the *Salmonella typhimurium* test strains employed, as well as non-mutagenic. The greatly decreased toxicity obtained with the $C_8$ to $C_{20}$ alkyl substituent of the compounds of the present invention was also observed in mice and rats. At intraperitoneal doses of from 3 to 30 mg. per kg. of body weight in rats, the $C_8$ to $C_{20}$ alkyl derivative produced no side effects, while at the same time giving marked anti-inflammatory responses in the carrageenan paw edema assay. The lower alkyl homologs produced lethargy, a drop in body temperature, and other undesirable actions at the same dosages. An acute oral toxicity, $LD_{50}$ (mice), difference of greater than 10-fold was obtained; the n-octadecyl homolog toxicity was greater than 2500 mg./kg. of body weight, the highest level assayed, while the methyl homolog had an $LD_{50}$ value of 258 mg./kg. of body weight. Even subcutaneously, the n-dodecylamino derivative had an $LD_{50}$ (mice) value of 138 mg./kg. of body weight, while the n-butylamino homolog was 44 mg./kg. and the methyl homolog was 35 mg./kg. of body weight.

For the purpose of treating pain, fever, and inflammation, the compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example, starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethyl-cellulose, methyl-cellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chaining aliphatic alcohols, for example heptadecaethyleneoxycetanol or condensation products of ethylene oxide with partial esters derived from fatty acids and a hexitol such as polyoxyethylene sorbitol mono-oleate, or condensation products of ethylene oxide with partial esters derived from fatty acid anhydrides and hexitol, for example polyoxyethylene sorbitan monooleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspension may contain a thickening agent, for example beeswax, hard paraffin or cetyl alcohol. Sweetening agents, such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the present invention may also be in the form of oil-in-water emulsions. The oil phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acid anhydrides and hexitol, for example sorbitan mono-oleate and condensation products of the said partial esters with ethylene oxide, for example polyoxyethylene sorbitan mono-oleate. The emulsions may also contain sweetening and flavouring agents.

Syrups and elixirs may be formulated with sweetening agents, for example glycerol, sorbitol or sucrose. Such formulations may also contain a demulcent, a preservative and flavouring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are coca butter and polyethylene glycols.

For topical use, creams, ointments, jellies, solutions or suspensions, etc. containing the anti-inflammatory agents are employed.

Dosage levels of the order of 20 mg. to 1 gram per day are useful in the treatment of the above indicated conditions. For example, inflammation is effectively treated and anti-pyretic and analgesic activity manifested by the administration of from about 0.3 to 60 milligrams of the compound per kilogram of body weight per day. Advantageously from about 2 mg. to about 30 mg. per kilogram of body weight and especially from about 4 mg. to about 20 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of Formula I may be prepared by techniques involving the condensation of a $C_8$-$C_{20}$ substituted amine, formaldehyde, and cyanacetic acid, as illustrated in the following reaction scheme:

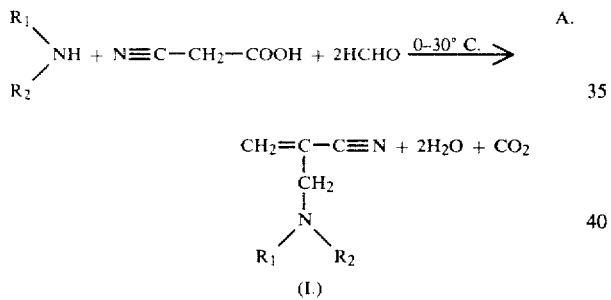

The compounds of Formula II. are obtained from the compounds of Formula I. by nucleophilic addition of an appropriately substituted amine, as illustrated in the following reaction scheme:

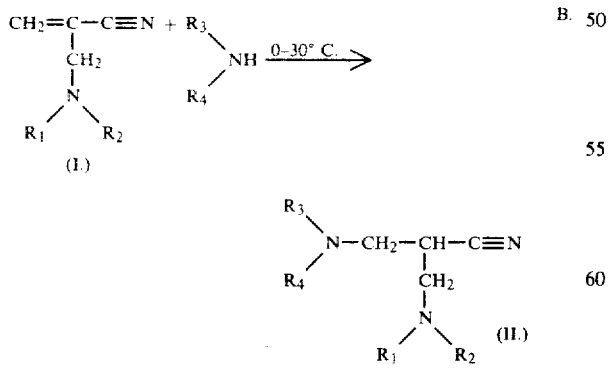

Generally, the reaction illustrated in A. above is run using equimolar quantities of a $C_8$-$C_{20}$ alkyl substituted amine and cyanacetic acid with two moles or more of formaldehyde in homogeneous solution, such as with dioxane. The initiation of product formation, usually beginning after 15 minutes is marked by evolution of carbon dioxide and completion obtained after three hours. Occasionally, reaction times as long as 30 hours at 25°-35° C. are required for total conversion. It is useful for good control to precool the cyanoacetic acid in dioxane solution to 5°-15° C., gradually add the substituted amine with the cold bath applied and finally the formaldehyde. After all has been added, the ice bath is removed and the solution allowed to warm.

The work-up involves stripping off the solvent at 40° C./15 mm., taking up the residue in ether and washing with cold aqueous 5% potassium carbonate followed by ice water. The ether solution is then dried over anhydrous magnesium sulfate, filtered and volatiles removed to an internal temperature of 40°-50° C. at 15 mm. The residue is further purified, preferably by fractional distillation under reduced pressure, or by recrystallization. Often, the quality is sufficiently high to permit use as isolated.

The 2-cyano-1,3-disubstituted propanes are prepared in accordance with the chemical scheme of equation B. above. For those products in which the $C_8$-$C_{20}$ alkyl substituted amino groups at the 1 and 3 carbon atoms of the 2-cyanopropanes are identical, a change in molar reactant ratios from 1 mole of $C_8$-$C_{20}$ alkyl substituted amine to 2 moles per mole of cyanoacetic acid and per 2 moles of formaldehyde will provide the compounds in one process step.

The sequence of steps may be postulated as depicted by equations A. and B. above, wherein

is simply a second mole of

where $R_1$ and $R_2$ are as above defined. Or, an excess of amine may be used to displace a more volatile substituent amine and a second mole caused to undergo nucleophilic addition to the unsaturated propenenitrile derivative, as illustrated by Example 4 below.

When

is to be different, then the unsaturated nitrile products of equation I may be dissolved in dioxane, mixed with a 5-25% molar excess of the compound

which may be previously dissolved in the same volume of water or dioxane, and allowed to stand at 20°-35° C.

until addition is complete. Disappearance of the double bond, as measured by a change in infrared absorption or loss of the vinyl protons in the nuclear magnetic resonance spectrum, is used to monitor the progress of the reaction. Dry, powdered potassium carbonate is then added to saturation and the mixture extracted with ether. After filtration of the separated organic phase and drying over anhydrous magnesium sulfate, the solvent is stripped and the residue purified by fractional distillation under reduced pressure.

The following examples will serve to illustrate preparation of the compounds and compositions of the present invention, without, however, limiting the scope thereof.

EXAMPLE 1

2-[(N-Methyl-N-n-octadecylamino)methyl]-2-propenenitrile

To a mixture of cyanacetic acid (2.6 g., 0.03 mole) and N-methyl-N-octadecylamine (8.4 g., 0.03 mole) in 25 ml. of dioxane at room temperature is added 38% aqueous formaldehyde (5.4 g., 0.06 mole) dropwise over about 2 minutes. The resultant mixture is then heated gently in a hot water bath until a clear solution is obtained and carbon dioxide is released vigorously (ca. 60° C. bath). When the evolution of carbon dioxide is complete, the mixture is allowed to cool, and the volatiles removed in vacuo to yield 9.2 g. of the substituted propenenitrile as an off-white solid.

Purification via chromatography on silica gel (methylene chloride eluant) yields the compound as a white solid, m.p. 37°-38° C.

EXAMPLE 2

2-[Di(n-nonyl)aminomethyl]-2-propenetrile

Cyanacetic acid (4.25 g., 0.05 mole), di(n-nonyl)amine (13.5 g., 0.05 mole), 38% aqueous formaldehyde (9.0 g., 0.1 mole) and dioxane (15 ml.) are reacted together as with the procedure of Example 1 above. The cooled mixture is then extracted well with ether, the combined ether extracts washed with 5% potassium carbonate solution, and dried over anhydrous powdered sodium sulfate, then filtered and concentrated in vacuo to 13.0 g. of an oily product of good purity. The compound is further purified by fractional distillation, b.p. 138°-140° C. (0.1 mm.).

The following compounds of Formula I are synthesized from the following substituted amines, cyanacetic acid, and formaldehyde, in accordance with the producedures of Examples 1 and 2 above:

| Amine | Product |
|---|---|
| N-(2-hydroxyethyl)-N- | 2-([N-(2-hydroxyethyl)-N- |
| n-octadecylamine | n-octadecylamino]methyl-2-propenenitrile |
| N-carboxymethyl-N-n-decylamine | 2-[(N-carboxymethyl-N-n-decylamino)methyl]-2-propenenitrile |
| N-carboethoxymethyl-N-n-tetradecylamine | 2-[(N-carboethoxymethyl-N-n-tetradecylamino)methyl]-2-propenenitrile |
| N-(3-carboxamidopropyl)-N-(2,2,6-trimethylheptyl)amine | 2-{[N-(3-carboxamidopropyl)-N-(2,2,6-trimethylheptylamino]methyl}-2-propenenitrile |
| N-trifluoromethyl-N-n-hexadecylamine | 2-[(N-trifluoromethyl-N-n-hexadecylamino)methyl]-2-propenenitrile |
| N-(3-methoxypropyl)-N-n-dodecylamine | 2-{[N-(3-methoxypropyl)-N-n-dodecylamino]methyl}-2-propenenitrile |
| N-cyclopentyl-N-n-dodecylamine | 2-[(N-cyclopentyl-N-n-dodecylamino)methyl]-2-propenenitrile |
| di(2,6-dimethyl-4-heptyl)amine | 2-{[di(2,6-dimethyl-4-heptyl)amino]methyl}-2-propenenitrile |
| N-n-octadecylamine | 2-[N-n-octadecylamino)methyl]-2-propenenitrile |
| N-n-tetradecylamine | 2-[(N-n-tetradecylamino)methyl]-2-propenenitrile 2-propenenitrile |

EXAMPLE 3

2-Cyano-N,N-dimethyl-N'-n-dodecyl-1,3-propanediamine

To a 5.5 g. (0.05 mole) of 2-(N,N-dimethylamino)-methyl-2-propenenitrile at 20° C. is added with stirring 9.0 g. (0.048 mole) of n-dodecylamine in portions over ca. 25 minutes. After stirring at ambient temperatures for several days, the reaction mixture is stripped under reduced pressure to remove any volatile impurities. There remains 12.8 g. of a pale yellow oil of good purity. Fractional distillation yields pure product, b.p. 163°-165° C. (0.4 mm.).

When the n-dodecylamine in the above reaction is replaced with an equivalent amount of 3-(2-methoxyethoxy)-propylamine, there is obtained 2-cyano-N,N-dimethyl-N'-[3-(2-methoxyethoxyy)propyl]-1,3-propanediamine, b.p. 122°-125° C. (0.13 mm.).

When the n-dodecylamine is replaced by an equivalent amount of t-octylamine, and the reaction mixture heated in an oil-bath at 80° C. until reaction is complete, there is obtained the t-octyl analog, 2-cyano-N,N-dimethyl-N'-t-octyl-1,3-propanediamine, b.p. 86.5°-87.5° C. (0.25 mm.).

The following compounds of Formula II are synthesized by addition of the following amines to the propenenitriles of Formula I:

| Propenenitrile of Formula I | Amine | 1,3-Propanediamine of Formula II |
|---|---|---|
| 2-[(N,N-dimethylamino)methyl]-2-propenenitrile | N-n-octadecylamine | 2-cyano-N,N-dimethyl-N'-n-octadecyl-1,3-propanediamine |
| 2-[(N,N-dimethylamino)methyl]-2-propenenitrile | N,N-di(n-dodecyl)amine | 2-cyano-N,N-dimethyl-N',N'-di(n-dodecyl)-1,3-propanediamine |
| 2-[N,N-di(n-butyl)amino]methyl-2-propenenitrile | N-n-tetradecylamine | 2-cyano-N,N-di(n-butyl)-N'-n-tetradecyl-1,3-propanediamine |
| 2-[(N-carboxymethyl-N-n-decyl-amino)methyl]-2-propenenitrile | N,N-di(n-hexyl)amine | 2-cyano-N,N-di(n-hexyl)-N'-carboxymethyl-N'-n-decyl-1,3-propanediamine |
| 2-[(N-methyl-N-n-octadecyl- | N,N-di(3-methoxy- | 2-cyano-N,N-di(3-methoxypropyl)- |

| Propenenitrile of Formula I | Amine | 1,3-Propanediamine of Formula II |
|---|---|---|
| amino)methyl]-2-propenenitrile | propyl)amine | N'-methyl-N'-n-octadecyl-1,3-propanediamine |
| 2-[(N-methyl-N-n-octadecylamino)methyl]-2-propenenitrile | N,N-diethanol amine | 2-cyano-N,N-di(2-hydroxyethyl)-N'-methyl-N'-n-octadecyl-1,3-propanediamine |
| 2-[(N-methyl-N-n-octadecylamino)methyl]-2-propenenitrile | tris-hydroxymethyl-aminomethane | 2-cyano-N-tris(hydroxymethyl)methyl-N'-methyl-N'-n-octadecyl-1,3-propanediamine |

EXAMPLE 4

2-Cyano-N,N'-di(n-decyl)-1,3-propanediamine

To stirred n-decylamine (47.2 g., 0.3 mole) at 20° C. is added dropwise 2-[(N,N-dimethylamino)methyl]-2-propenenitrile (11.0 g., 0.1 mole) over a 3 minute period. The reaction mixture, protected from moisture with an Ascarite drying tube, is stirred at room temperature an additional three hours. It is then heated at 80° C. for 48 hours. The mixture is fractionally distilled under reduced pressure to remove a small amount of unreacted, excess n-decylamine, 2-cyano-N-(n-decyl)-N',N'-dimethyl-1,3-propanediamine as byproduct, and finally the product, 2-cyano-N,N'-di(n-decyl)-1,3-propanediamine.

The following compounds of Formula II may be prepared from the following substituted amines in accordance with the procedures of Example 4 above:

| Amine | Product of Formula II |
|---|---|
| N-methyl-N-n-octadecylamine | 2-cyano-N,N'-dimethyl-N,N'-di(n-octadecyl)-1,3-propanediamine |
| N,N-di(n-dodecyl)amine | 2-cyano-N,N,N',N'-tetradodecyl-1,3-propanediamine |
| N-(3,3-dimethylcyclohexyl)-N-n-tetradecylamine | 2-cyano-N,N'-di(3,3-dimethylcyclohexyl)-N,N'-di(n-tetradecyl)1,3-propanediamine |
| N-[3-(2-methoxy-ethoxy)propyl]-N-n-octadecylamine | 2-cyano-N,N'-di[3-(2-methoxyethoxy)propyl]-N,N'-di (n-octadecyl)-1,3-propanediamine |
| N-n-butyl-N-n-tetradecylamine | 2-cyano-N,N'-di(n-butyl)-N,N'-di(n-tetradecyl)-1,3-propanediamine |
| N-(2-ethylhexyl)-N-n-decylamine | 2-cyano-N,N'-di(2-ethylhexyl)-N,N'-di(n-decyl)-1,3-propanediamine |
| N-(2-hydroxyethyl)-N-n-nonadecylamine | 2-cyano-N,N'-di(2-hydroxyethyl)-N,N'-di(n-nonadecyl)-1,3-propanediamine |
| N-(2,2-difluoroethyl)-N-n-hexadecylamine | 2-cyano-N,N'-di(2,2-difluoroethyl)-N,N'-di(n-hexadecyl)-1,3-propanediamine |
| N-methoxycarbonylmethyl-N-n-nonadecylamine | 2-cyano-N,N'-di(methoxycarbonylmethyl)-N,N'-di (n-nonadecyl)-1,3-propanediamine |

EXAMPLE 5

2-[(N,N-dimethyl-N-n-octadecylammonio)methyl]-2-propenenitrile chloride

A mixture of 2-[N-methyl-N-n-octadecylamino)methyl]-2-propenitrile (17.4 g., 0.05 mole) and methyl chloride (5.0 g., 0.1 mole) in 150 ml. of acetone is heated at 60° C. for 6 hours in a Parr bomb. The reaction mixture is cooled to +15° C. and the precipitated solids removed by suction filtration, then washed with dry acetone and dried. The product is further purified by recrystallizations from acetone-ethyl alcohol mixtures or by solution in 2-propanol followed by slow precipitation with ether.

EXAMPLE 6

2-[N-benzyl-N,N-di(nonyl)ammonio]methyl-2-propenenitrile chloride

A mixture of 2-[N-dinonylamino)methyl]-2-propenenitrile (3.3 g., 0.01 mole) and benzyl chloride (2.5 g., 0.02 mole) in 10 ml. of acetone is heated at reflux for 16 hours. The solution is cooled in an ice bath to +15° C. and kept cold for 4 hours. The precipitated product is removed by suction filtration, washed with cold acetone and dried. It is recrystallized from acetone.

EXAMPLE 7

2-Cyano-N,N-dimethyl-N'-methyl-N'-n-octadecyl-1,3-propanediamine dihycrochloride 2-Cyano-N,N-dimethyl-N'-methyl-N'-n-octadecyl-1,3-propanediamine (1 g.) is dissolved in 5 ml. of 2-propanol. With cooling in an external bath a stream of dry, hydrogen chloride gas is introduced until saturation. The solvent is stripped in vacuo and the residue triturated with ether; suction-filtration is used to separate the solids followed by a cold ether wash. The dihydrochloride salt is further purified by recrystallization from 2-propanol-ether mixture.

EXAMPLE 8

2-[(N-methyl-N-n-octadecylamino)methyl]-2-propenenitrile propionic acid salt

A solution of 2[(N-methyl-N-n-octadecylamino)methyl]-2-propenenitrile (1.7 g., 0.005 mole) in 10 ml. of acetone is mixed with propionic acid (0.41 g., 0.0055 mole). The solvent is stripped in vacuo, and the residue is dissolved in a small volume of ether. Low boiling petroleum ether is gradually added until the ice cold solution became turbid. After standing at 10° C. for 12 hours the product is removed by suction filtrations and then washed with cold petroleum ether followed by drying at ambient temperature.

EXAMPLE 9

A mixture of 250 parts of 2-[(N-n-octadecylamino)-methyl]-2-propenenitrile hydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen and mixed with 3.8 parts of magnesium stearate. They are then compressed into tablets suitable for oral administration.

The compound used in the foregoing example may be replaced by 25, 100, or 500 parts of the propenenitrile to product tablets suitable for oral administration as an anti-inflammatory, antipyretic and/or analgesic according to the method of this invention.

EXAMPLE 10

A mixture of 50 parts of the propionic acid salt of 2-[(N-methyl-N-n-octadecylamino)methyl]-2-propenenitrile, 3-parts of the calcium salt of lignin sulphonic acid, and 237 parts of water is ball-milled until the size of substantially all particles of the compound is less than 10 microns. The suspension is diluted with a solution containing 3 parts of the butyl ester of p-hydroxy-benzoic acid in 300 parts of water. There is thus obtained an aqueous suspension suitable for oral administration for therapeutic purposes.

EXAMPLE 11

A mixture of 250 parts of 2-[(N-hexyl-N-n-pentadecylamino)methyl]-2-propenenitrile succinate, 200 parts of maize starch and 30 parts of alginic acid is mixed with a sufficient quantity of a 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 12

A mixture of 500 parts 2-[N-(2-methoxyethyl)-N-n-octadecylamino]methyl-2-propenenitrile hydrochloride, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 13

(1) Tablets - 10,000 scored tablets for oral use, each containing 100 mg. of propenenitrile, are prepared from the following ingredients.

| | |
|---|---|
| 2-[(N-methyl-N-n-octadecylamino)methyl]-2-propenenitrile hydrochloride | 1000 |
| Starch, U.S.P. | 350 |
| Talc, U.S.P. | 250 |
| Calcium Stearate | 35 |

The powdered hydrochloride salt is granulated with a 4% w./v. aqueous solution of methylcellulose U.S.P. (1500 cps.). To the dried granules is added a mixture of the remainder of the ingredients and the final mixture compressed into tablets of proper weight.

(2) Capsules - 10,000 two-piece hard gelatin capsules for oral use, each containing 50 mg. of the propenenitrile hydrochloride are prepared from the following ingredients:

| | |
|---|---|
| 2-[(N-methyl-N-n-octadecylamino)methyl]-2-propenenitrile hydrochloride | 500 |
| Lactose, U.S.P. | 1000 |
| Starch, U.S.P. | 300 |
| Talc, U.S.P. | 65 |

| -continued | |
|---|---|
| Calcium Stearate | 25 |

The powdered hydrochloride salt is mixed with the starch-lactose mixture followed by the talc and calcium stearate. The final mixture is then encapsulated in the usual manner. Capsules containing 10 and 25 mg. of the hydrochloride salt are also prepared by substituting 100 and 250 gm. for 500 gm. in the above formulation.

(3) Soft elastic capsules - One piece soft elastic capsules for oral use, each containing 50 mg. of 2-[(N-methyl-N-n-octadecylamino)methyl]-2-propenenitrile hydrochloride are prepared in the usual manner by first dispersing the powdered active material in sufficient corn oil to render the material capsulatable.

(4) Aqueous suspension—An aqueous suspension for oral use containing in each 5 ml., 200 mg. of propenenitrile is prepared from the following ingredients:

| | GM |
|---|---|
| 2-[(N-methyl-N-n-octadecylamino)methyl]-2-propenenitrile hydrochloride | 400 |
| Methylparaben, U.S.P. | 7.5 |
| Propylparaben, U.S.P. | 2.5 |
| Saccharin sodium | 12.5 |
| Glycerin, 3000 ml. | |
| Tragacanth Powder | 10 |
| Orange Oil Flavor | 10 |
| F.D. and C. Orange Dye | 7.5 |

What is claimed is:

1. A compound of the formula

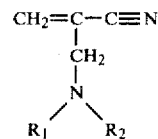

wherein:

$R_1$ is straight or branched $C_{12}$–$C_{20}$ alkyl;

$R_2$ is selected from the group consisting of hydrogen; straight or branched $C_1$–$C_{20}$ alkyl; hydroxy $C_{1-4}$ alkyl; $C_{1-4}$ alkoxy $C_{1-4}$ alkyl; halo $C_{1-4}$ alkyl; and $C_{3-8}$ cycloakyl;

or a pharmaceutically acceptable acid addition salt thereof.

2. A compound according to claim 1 which is 2-[(N-n-octadecylamino)methyl]-2-propenenitrile.

3. A compound according to claim 1 which is 2-[(N-methyl-N-n-octadecylamino)methyl]-2-propenenitrile.

4. A compound according to claim 1 which is 2-[(N-hexyl-N-n-pentadecylamino)methyl]-2-propenenitrile.

5. A method of treating sympotms of pain, fever, and inflammation, comprising administering to a patient in need of such treatment an effective amount of a compound of the formula:

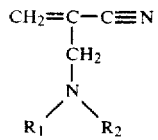

wherein

R$_1$ is straight or branched C$_8$–C$_{20}$alkyl;

R$_2$ is selected from the group consisting of hydrogen; straight or branched C$_1$–C$_{20}$ alkyl; hydroxy C$_{1-4}$ alkyl; C$_{1-4}$alkoxy C$_{1-4}$ alkyl; halo C$_{1-4}$ alkyl; and C$_{3-8}$ cycloalkyl;

or a pharmaceutically acceptable acid addition salt thereof.

6. A pharmaceutical composition for treating sympotms of pain, fever, and inflammation, comprising a pharmaceutically acceptable, non-toxic carrier, and an effective amount of a compound of the formula:

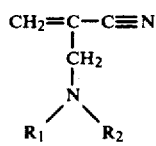

wherein

R$_1$ is straight or branched C$_{12}$–C$_{20}$ alkyl;

R$_2$ is selected from the group consisting of hydrogen; straight or branched C$_1$–C$_{20}$ alky; hydroxy C$_{1-4}$ alkyl; C$_{1-4}$ alkoxy C$_{1-4}$alkyl; halo C$_{1-4}$ alkyl; and C$_{3-8}$ cycloalkyl;

or a pharmaceutically acceptable acid addition salt thereof.

7. A composition according to claim 6 wherein the compound is
2-[(N-methyl-N-n-octadecylamino)methyl]-2-propenenitrile.

8. A composition according to claim 6 wherein the compound is
2-[(N-hexyl-N-n-pentadecylamino)methyl]-2-propenenitrile.

9. A composition according to claim 6 wherein the compound is
2-[(N-n-octadecylamino)methyl]-2-propenenitrile.

10. A method according to claim 5 wherein the compound is
2-[(N-n-octadecylamino)methyl]-2-propenenitrile.

* * * * *